(12) United States Patent
Zolli (10) Patent No.: US 8,721,581 B2
(45) Date of Patent: May 13, 2014

(54) CAPSULE FRIENDLY TIPS FOR PHACOEMULSIFICATION AND FOR IRRIGATION / ASPIRATION

(71) Applicant: Christine Lydie Zolli, Oldwick, NJ (US)

(72) Inventor: Christine Lydie Zolli, Oldwick, NJ (US)

( * ) Notice: Subject to any disclaimer, the term of this patent is extended or adjusted under 35 U.S.C. 154(b) by 0 days.

(21) Appl. No.: 13/845,356

(22) Filed: Mar. 18, 2013

(65) Prior Publication Data
US 2013/0226152 A1    Aug. 29, 2013

Related U.S. Application Data (63) Continuation-in-part of application No. 12/794,715, filed on Jun. 4, 2010, now Pat. No. 8,398,578.

(51) Int. Cl.
*A61N 1/30* (2006.01)

(52) U.S. Cl.
USPC ............ 604/19; 604/239; 604/275; 604/540; 606/107

(58) Field of Classification Search
USPC ................... 604/19, 275, 540, 239; 606/107
See application file for complete search history.

(56) References Cited

U.S. PATENT DOCUMENTS

| 4,657,772 A | 4/1987 | Kocak |
| 6,126,629 A | 10/2000 | Perkins |
| 8,398,578 B1 * | 3/2013 | Zolli ............................ 604/19 |

* cited by examiner

*Primary Examiner* — Theodore Stigell
(74) *Attorney, Agent, or Firm* — Hess Patent Law Firm LLC; Robert J. Hess (57) ABSTRACT

A surgical tool that includes a tip with a smooth, rounded edges and free of any sharp edges. The tip may have pores on its top, but none on the underside of its base. The distal end may have an open port with micro wires that form a Maltese cross shape. The distal end may be instead closed with protrusions spaced from each other by gaps or recesses.

4 Claims, 10 Drawing Sheets

CAPSULE FRIENDLY TIPS FOR PHACOEMULSIFICATION AND FOR IRRIGATION / ASPIRATION

CROSS-REFERENCE TO COPENDING PATENT APPLICATIONS

The present application is a continuation-in-part utility patent application from U.S. utility patent application Ser. No. 12/794,715 filed Jun. 4, 2010, now U.S. Pat. No. 8,398,578 issued Mar. 19, 2013, which in turn claims the benefit of priority from U.S. provisional patent application Ser. No. 61/184,399 filed Jun. 5, 2009.

BACKGROUND OF THE INVENTION

1. Field of the Invention

One aspect of the invention relates to surgical tools in the form of an elongated shaft and tip suited for use in phacoemulsification surgical instruments and irrigation-aspiration instruments.

2. Discussion of Related Art

Conventional phacoemulsification tips are sharp and have an overly large port that admits the eye capsule in a blink-of-an-eye. The eye capsule, when sucked into the overly large port, puckers and rips to produce rapidly widening tear lines through which vitreous prolapses, which often leads to vitreous loss. Therefore, the use of such conventional phacoemulsification tips that are sharp with the overly large port run the risk of causing capsule ruptures, which is a very serious intraoperaive, i.e., surgical, complication. As an alternative, femto lasers are used (sometimes referred to as femtosecond lasers) to assist cataract surgery procedures.

In an article entitled "Femtosecond Laser Cataract Surgery: Advantages Await Clinical Trial Results" by James Brice and published Nov. 26, 2012, Femtosecond laser cataract surgery are discussed. Excerpts from the article are in the following seven paragraphs.

Femtosecond lasers promise to literally to cut a new edge in terms of the precision and accuracy of incisions made during cataract surgery, according to Calvin Roberts, MD, chief medical officer of Bausch+Lomb. Bausch+Lomb is 1 of 5 companies that produce US Food and Drug Administration-cleared femtosecond laser surgical systems.

Surgery using handheld instruments is the current standard for treating cataracts, which are responsible for nearly 50% of blindness worldwide. The success of this approach depends to a great extent on the surgeon's skill and experience. About 10 million cataract surgeries are performed annually worldwide, according to the World Health Organization. Many of those patients could benefit from a conversion to femtosecond lasers guided by ultra-high-resolution 3-dimensional optical coherence tomography (OCT).

Femtosecond lasers are well suited for cataract surgery because of their ability to tightly focus energy to produce precise surgical incisions, Dr. Roberts said. Cuts of a uniform depth into the lens are possible. The disruptive heat associated with current laser technology is reduced as the laser pulses once every one-trillionth of a second. The ability to focus such energy allows the surgeon to cut deeply on a single plane without collateral damage, he said.

Results of preliminary research are promising. Femtosecond lasers produce continuous anterior incisions for capsulorrhexis that are twice as strong and more than 5 times as precise in size and shape as manual incisions, according to a 2010 study by Palanker and colleagues at Stanford University School of Medicine, Stanford, Calif.

Palanker and colleagues' research revealed that segmenting and softening the lens with a femtosecond laser simplifies its emulsification and removal. Three-dimensional cutting of the cornea takes advantage of internal pressure in the eye to create self-sealing incisions, and it allows exact placement of the limbal-relaxing incisions, often performed in the same procedure, that are used to treat astigmatism.

Friedman and colleagues, also at Stanford University School of Medicine, measured the accuracy of an OCT-guided femtosecond laser for cutting specified circles and curved incisions and compared it with manually created capsulorhexis in a small human study. Deviation from the intended diameter of the resected capsule disk was 29 (±26 μm) for the laser technique and 337 μm (±258 μm) for manual incisions. Mean deviations from circularity were 6% for the laser and 20% for manual incisions.

The advantage conferred by this precision can be applied to corneal incisions, anterior capsulotomy, and lens softening and fragmentation before aspiration, noted Roger F. Steinert, MD, chair of ophthalmology at the University of California, Irvine, School of Medicine. "You can't do these things repeatedly or dependably when you are operating manually with a blade," he said.

Indeed, the safety benefits of femtosecond laser-assisted cataract surgery are mentioned in a further article entitled "Technique yields safety benefits Femtosecond laser-assisted cataract study procedure minimizes corneal trauma" by Cheryl Guttman Krader, reviewed by Zoltan Z Nagy, MD, PhD, and published in Opthalmology Times on Dec. 1, 2012. The article mentions that the increased safety of the femto [second] laser procedure in this study might be attributed to the user of less ultrasound energy during phacoemulsification and was associated with less early corneal edema and better corneal endothelial cell function compared with standard cataract surgery. Average phaco power was reduced by as much as 51% compared to standard cataract surgery and the effective phaco time was reduced by as much as 43% compared to standard cataract surgery.

An intraocular lens, or IOL, is an artificial lens made of plastic, silicone or acrylic that performs the function of the eye's natural lens. Most of today's IOLs are less than a quarter of an inch in diameter and soft enough to be folded so they can be placed into the eye through a very small incision.

There is a need to reduce a risk of causing capsule ruptures, i.e., by avoiding the use of conventional phacoemulsification tips that are sharp and that have an overly large port. That is, there is a need for phacoemulsification tips that are safe in the sense that they are not as likely to cause capsule ruptures. That is, the surgical tool should be "capsule friendly" to lessen the likelihood of creating capsule ruptures during their use in phacoemulsification surgical procedures or in irrigation-aspiration applications of the eye.

There is also a need to score and break-up glossy, coagulated walls, whose glossy, coagulated state resulted from impingement by a laser energy beam during the course of Femtosecond laser-assisted cataract surgery.

SUMMARY OF THE INVENTION

One aspect of the invention resides in "capsule friendly" tips suited for use with phacoemulsification type machines and with aspiration-irrigation instruments. Such "capsule friendly" tips achieve safe removal of cataract fractions without sucking in iris tissue or pulling in and thus rupturing the capsule. The "capsule friendly" tips are constructed so only the aspiration of soft cortex occurs while irrigating the area.

One embodiment resides in a mulberry tip that has protrusions configured to collectively and cooperatively engage with epinucleus cortical material so as, under manual pressure and guidance, to divide cortical fibers of the epinucleus cortical material. The mulberry tip being secured to a hollow shaft of an aspiration-irrigation tool in an airtight manner that is sufficiently tight for a suction force imparted into the hollow of the hollow shaft to suck the divided cortical fibers into the port and then flow through the hollow of the base to reach the hollow of the hollow shaft. Neighboring ones of the protrusions are separated from each other by gaps or recesses. Each of the protrusions have curved external surfaces entirely free of sharp edges. Both the hollow shaft and the hollow base are constructed of materials sufficient to avoid their collapse upon being subjected to the suction force that is of a magnitude necessary for the divided cortical fibers to suck into the port.

Still another embodiment resides in a hollow tip having a base that extends between proximal and distal ends, with the distal end terminating into a port crossed by micro wires in a shape of a Maltese cross. The proximal end is configured to fit to a hollow shaft in an airtight manner. The airtight manner is sufficiently tight for a suction force imparted into the hollow of the hollow shaft to suck divided cortical fibers of an epinucleus cortical material into the open port about the micro wires and then flow through the hollow of the base to reach the hollow of the hollow shaft. Both the hollow shaft and the hollow base are constructed of materials sufficient to avoid their collapse upon being subjected to the suction force that is of a magnitude necessary for the divided cortical fibers to suck into the open port around the micro wires.

BRIEF DESCRIPTION OF THE DRAWING

For a better understanding of the present invention, reference is made to the following description and accompanying drawings, while the scope of the invention is set forth in the appended claims.

DETAILED DESCRIPTION OF THE INVENTION

The tips of each of the embodiments include surgical hand piece tips that are suited for ultrasonic phacoemulsification (U-Phaco) type applications, irrigation/aspiration (I/A) type applications or both types of applications.

Kugeln Tip 60, 62, 64

Figure 1:
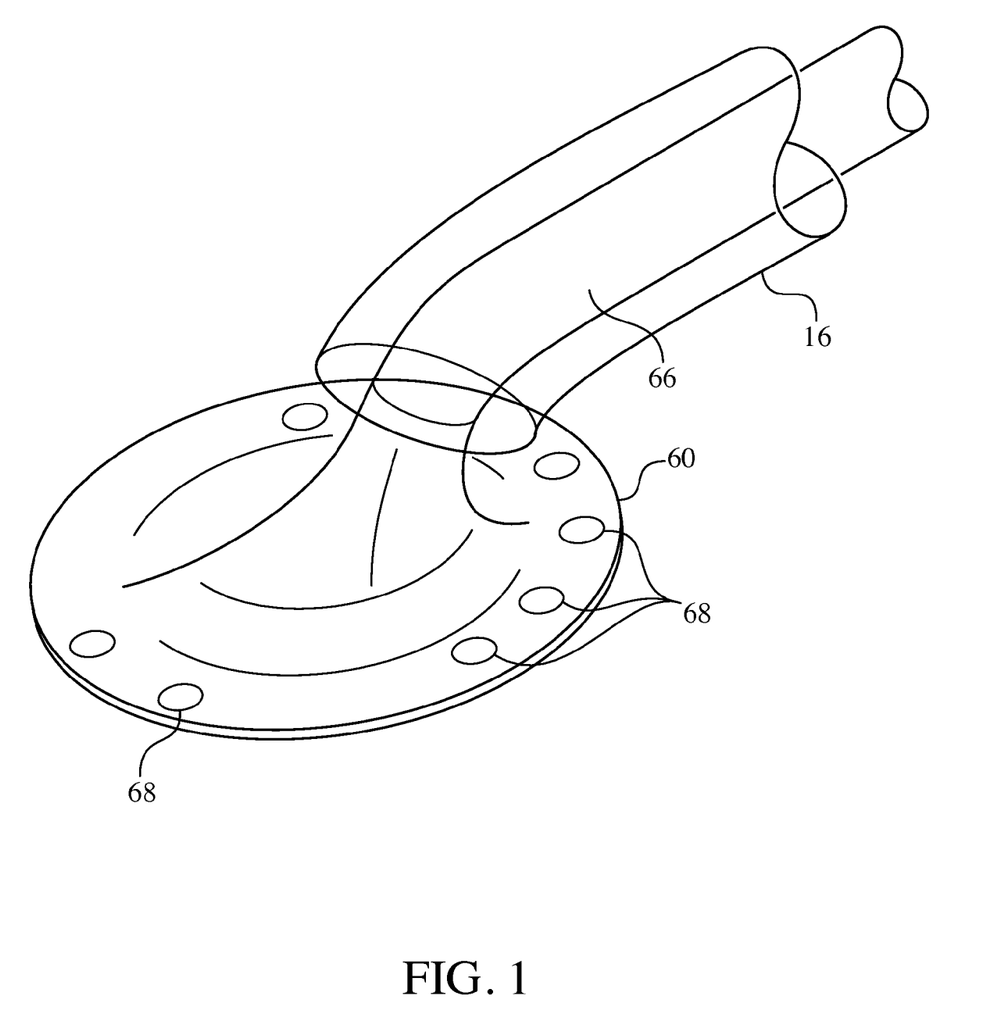
FIG. 1 is an isometric view of a funnel style kugeln tip embodiment in accordance with the invention in which an irrigation/aspiration shaft or needle curves to terminate into a funnel shape with pores directed backward to constitute a distal tip of an irrigation/aspiration surgical hand piece.
Figure 2:
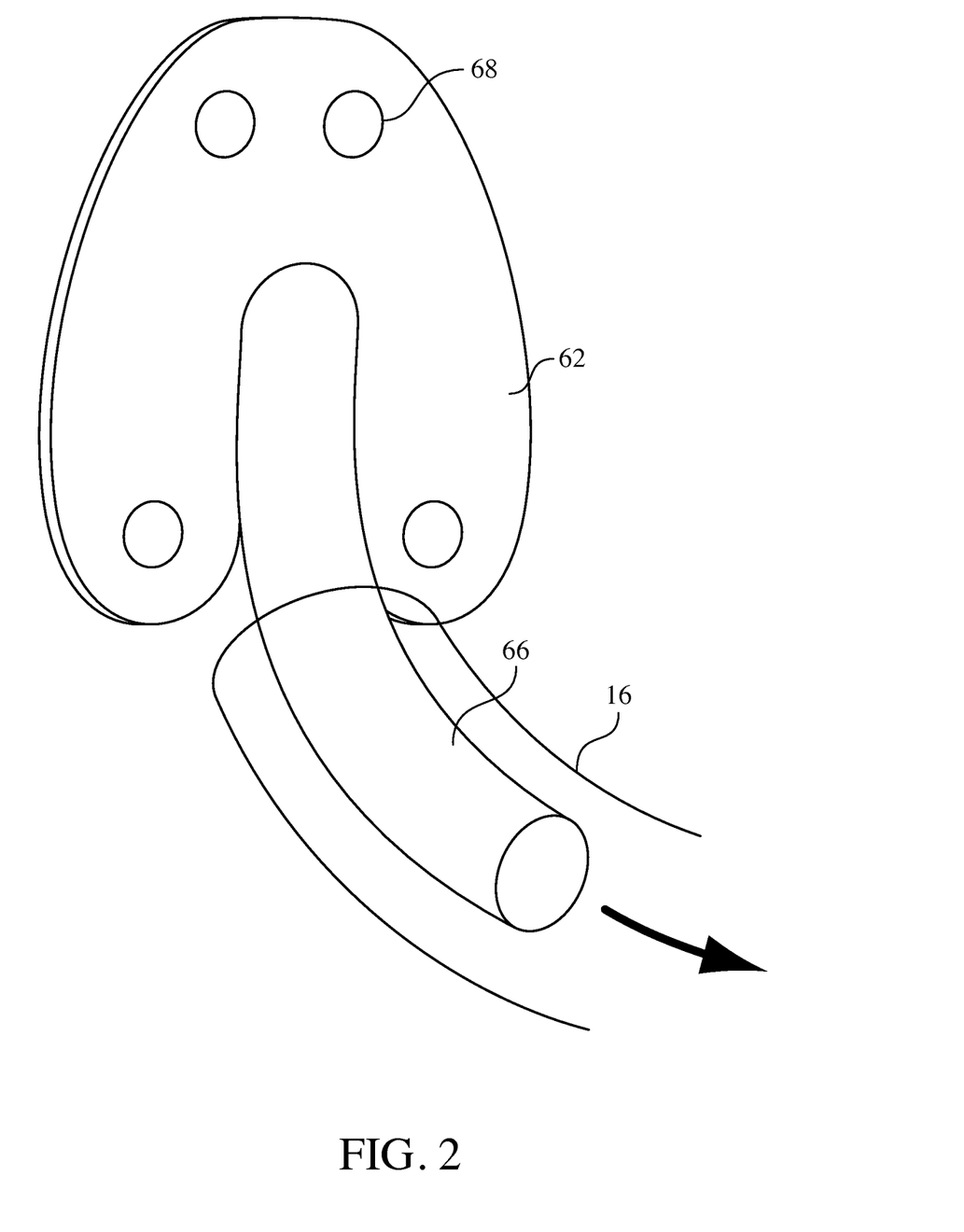
FIG. 2 is an isometric view of a horseshoe style kugeln tip embodiment in accordance with the invention in which an irrigation/aspiration shaft or needle curves to terminate into a horseshoe shape with pores directed backward to constitute a distal tip of an irrigation/aspiration surgical hand piece.
Figure 3:
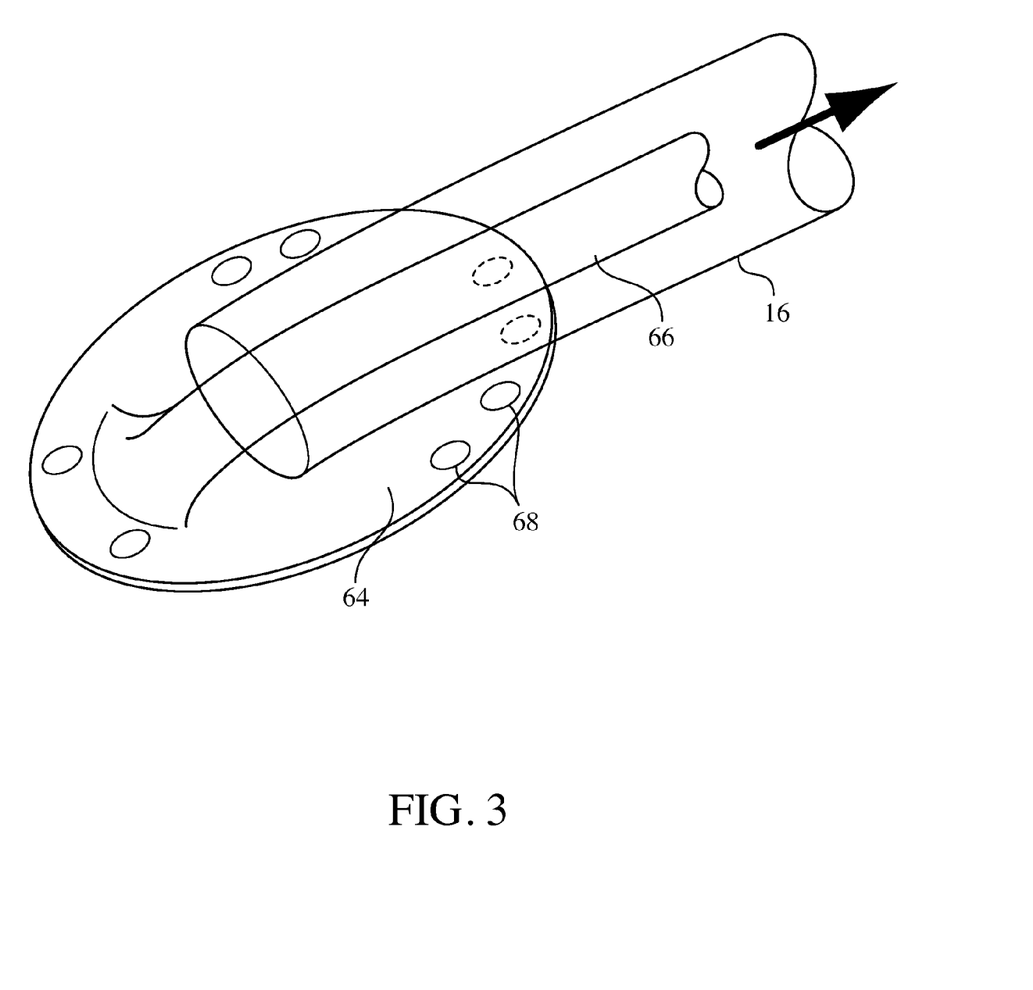
FIG. 3 is an isometric view of an oblong "Retro" style kugeln tip embodiment in accordance with the invention with longer backward reach in which an irrigation/aspiration shaft or needle curves to terminate into a oblong shape with pores directed backward to constitute a distal tip of an irrigation/aspiration surgical hand piece.

Turning to FIGS. 1-3, kugeln tips in accordance with different embodiments of the invention are shown each with a face with pores directed backward toward the surgeon to facilitate the removal of hard-to-get cortex under the port of entry, which is usually the 12 o'clock cortex.

In the case of FIG. 1, a funnel type kugeln tip is shown having a circular disc shaped globe 60 and an irrigation/aspiration shaft or needle 66 that extends within an infusion sleeve 16. The shaft or needle 66 terminates into a funnel shape that diverges at a transition into a face of the circular disc shaped globe 60. The pores 68 are directed backward and arranged in the face of the circular disc shaped globe 60 on the same side of the circular disc shaped globe 60 where the shaft or needle 66 funnels into the circular disc shaped globe 60. There are no pores on the opposite side of the circular disc shape globe 60.

In the case of FIG. 2, a horseshoe style kugeln tip is shown with a horseshoe shaped globe 62 and an irrigation/aspiration shaft or needle 66 that extends within an infusion sleeve 16. The shaft or needle 66 terminates into the horseshoe shaped globe 62. The pores 68 are directed backward in the horseshoe shaped globe 62 on the same side of the horseshoe shaped globe 62 from which approaches the shaft or needle 66 to reach the horseshoe shaped globe 62. There are no pores on the opposite side of the horseshoe shaped globe 62.

In the case of FIG. 3, an oblong "Retro" style kugeln is shown having an oblong globe 64 with a longer backward reach that in the case of the embodiments of FIGS. 1 and 2. The irrigation/aspiration shaft or needle 66 of FIG. 3 extends within an infusion sleeve 16 and terminates into the oblong globe 64. The oblong globe 64 has pores 68 that are directed backward on the same side of the oblong globe 64 that the shaft or needle 66 reaches the oblong globe 64. There are no pores on the opposite side of the oblong globe 64.

Figures 4, 5:
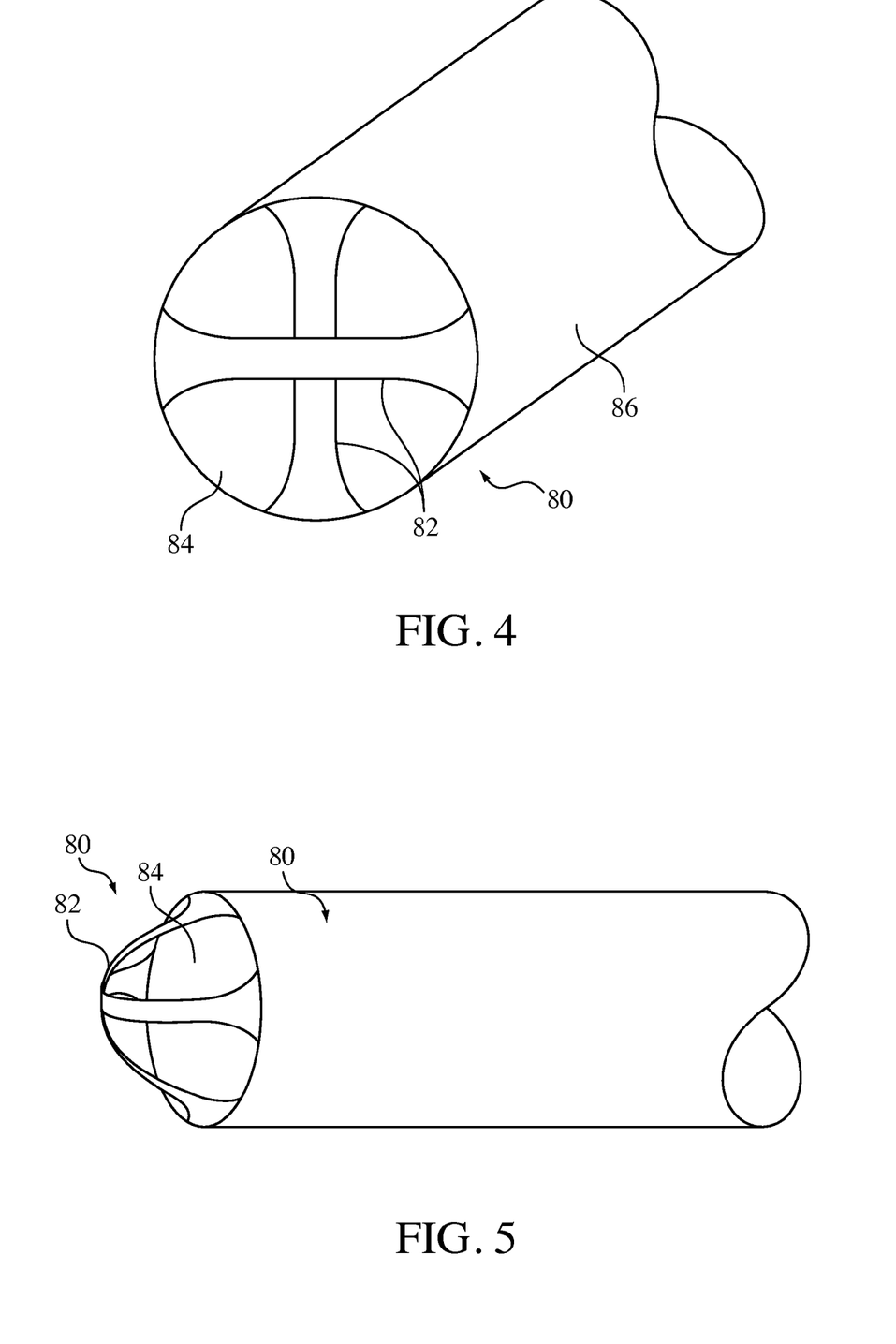
FIG. 4 is an isometric end view of a cross-bun or Maltese cross tip embodiment in accordance with the invention.
FIG. 5 is an isometric side view of a cross-bun or Maltese cross tip embodiment in accordance with FIG. 4.

Turning to FIGS. 4-5, the cross-bun or Maltese cross guard tips 80 resemble conventional U-Phaco and I/A tips the most out of all the embodiments and thus are likely the easiest to retool an existing tip manufacturing facility and thus the easiest for a conventional tip manufacturer to produce. Both U-Phaco and I/A type cross-bun or Maltese cross guard tips 80 look somewhat alike in that the aspiration port of each is located dead front and each has a built-in guard that is all one-piece with the tip.

The globe of the tip of the cross-bun or Maltese cross type is constituted by a hollow base 86 the extends between proximal and distal ends with two wire arms 82 made of fine smooth micro wires that straddle crosswise the port 84 at the distal end of the hollow base 86. They minimally bulge to appear slightly rounded and not sharp and connect to the edges of the port widened a bit, as if in shape of a Maltese cross. The two wire arms 82 cross at 90 degrees across the port 84, thereby dividing the port 84 into four smaller entrances that are each too small for the capsule to enter. The emulsified matter, however, flow faster around the wires, but then quickly join together to flow the full sized channel downstream of the wire part of he port to continue to be aspirated in accordance with the flow dynamics of conventional tips. This cross-bun or Maltese cross type of tip may be considered that of a shaft tip with the aspiration prevented by wire guards from sucking in the capsule and iris.

The proximal end of the cross-bun or Maltese cross type tip is configured to fit to a hollow shaft in an airtight manner. The airtight manner is sufficiently tight for a suction force imparted into the hollow of the hollow shaft to suck divided cortical fibers of an epinucleus cortical material into the open distal end around the micro wires and then flow through the hollow of the base to reach the hollow of the hollow shaft. Both the hollow shaft and the hollow base are constructed of materials sufficient to avoid their collapse upon being subjected to the suction force that is of a magnitude necessary for the divided cortical fibers to suck into the open distal end around the micro wires.

Figure 6:
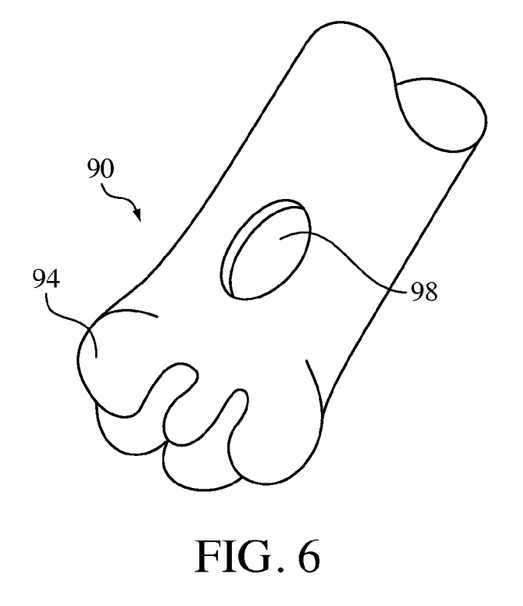
FIG. 6 is an isometric view of a mulberry tip in accordance with a straight shaft embodiment of the present invention.
Figure 7:
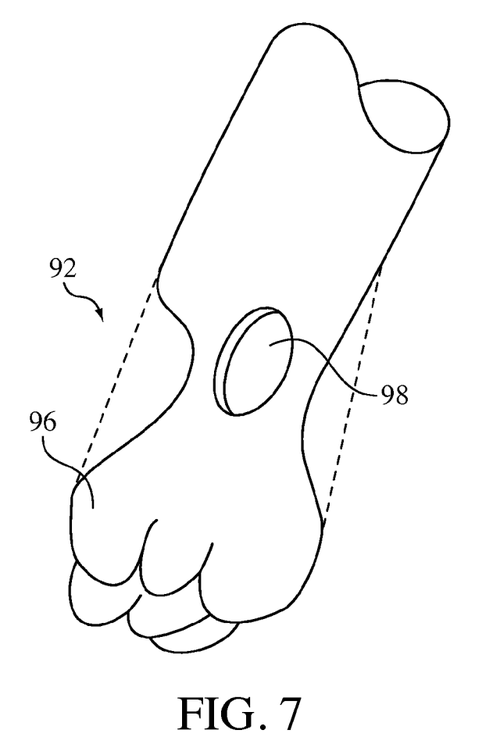
FIG. 7 is an isometric view of a mulberry tip in accordance with an indented shaft embodiment of the present invention.
Figure 8:
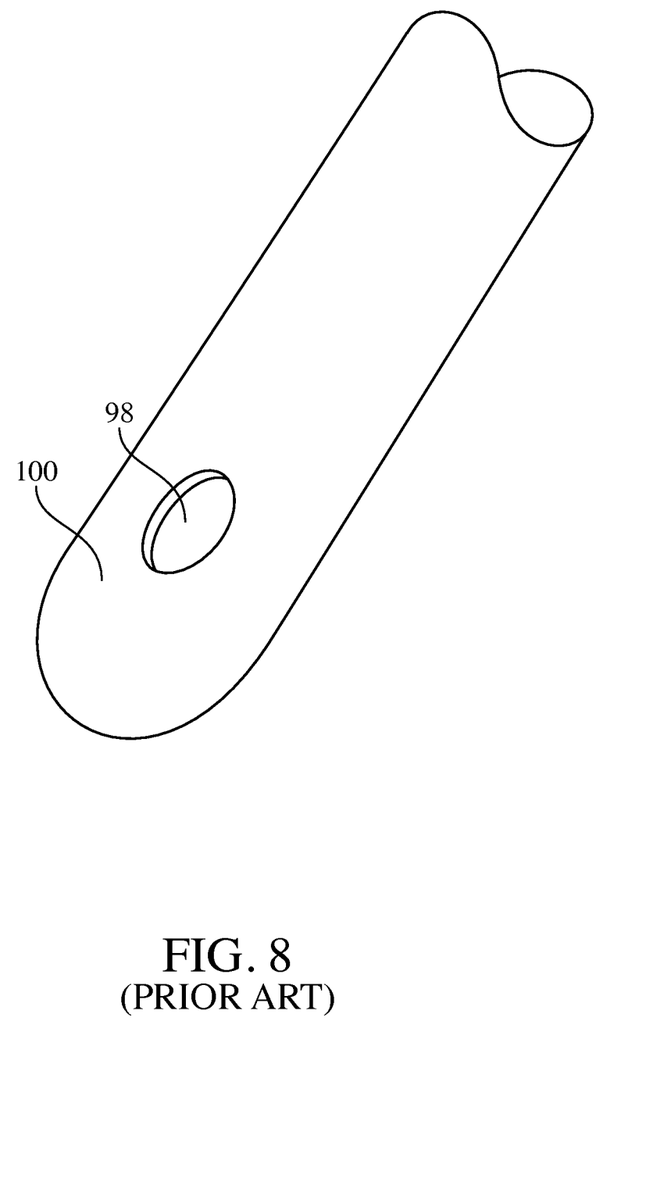
FIG. 8 is an isometric view of a conventional regular, rounded phacoemulsification tip.

Turning to FIGS. 6 and 7, two types of mulberry tips 90, 92 are shown, i.e., FIG. 7 is for a straight phaceoemuslfication shaft and FIG. 8 is for an indented phacoemulsification shaft. The size of the shaft for each type of mulberry tip 90, 92 is the same as that of a shaft of a conventional phacoemulsification rounded tip 100 of FIG. 9. The conventional phacoemulsification rounded tip 100 in this example has an end that is to smooth and thus just compresses the cortex material to shrivel it up so it could be aspirated better.

Each mulberry tip 90, 92 has a respective rounded surfacew protrustions 94, 96 separated from each other by gaps or recesses 95. The rounded surface protrusions 94, 96 are configured to engage epinucleus cortical material to work as a "battering ram" to divide cortical fibers so they can become dislodged and be aspirated with more ease than for conventional aspiration/irrigation tips 100 of FIG. 9. For instance, the rounded surface protrusions 94, 96 may take the form of a plurality of rounded protrusions that extend in a direction of elongation of the shaft (from which the mulberry tip extends). The rounded protrusions may be arranged concentric with a center axis of the tip and may be arranged in a symmetrical manner.

Further, there is a suction port 98 (hole, port or opening) for aspiration that should be sized to prevent sucking in the capsule during aspiration. The smooth, rounded surfaces of the tips form no regions of sharpness that might otherwise cut into the capsule during aspiration. For instance, there are intersecting planar surfaces in such smooth, rounded surfaces of the tips.

The mulberry tip 90, 92 of the present invention is fitted onto a hollow aspiration tube 112 of a conventional aspiration-irrigation instrument or handpiece for removal of the cortex through aspiration, which removal may or may not be in conjunction with Femto[second] laser-assisted cataract surgery.

Figure 9:
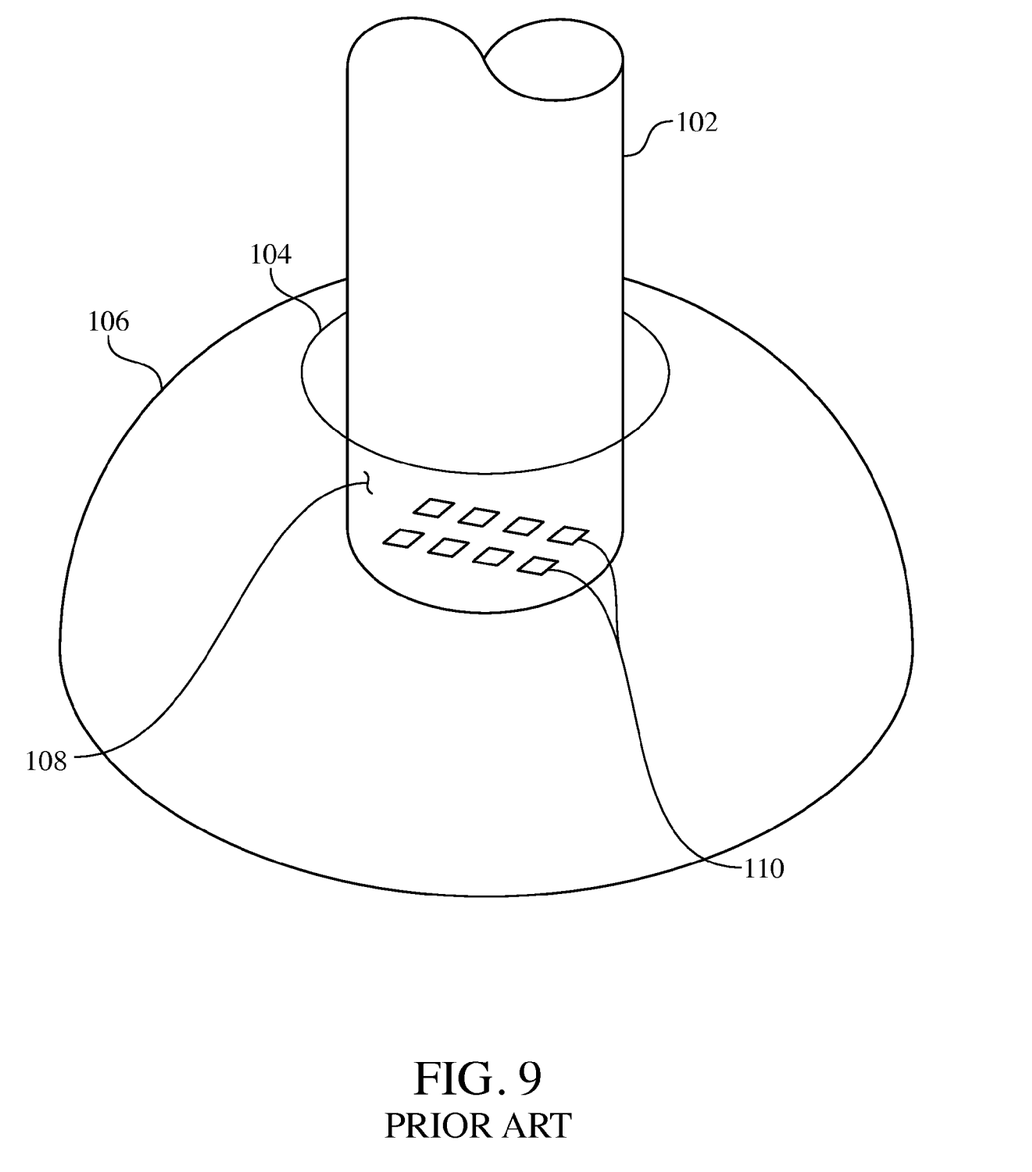
FIG. 9 is an isometric view of a cataract with the nucleus of the lens being broken up by energy delivered by a laser beam in accordance with conventional techniques.
Figure 11:
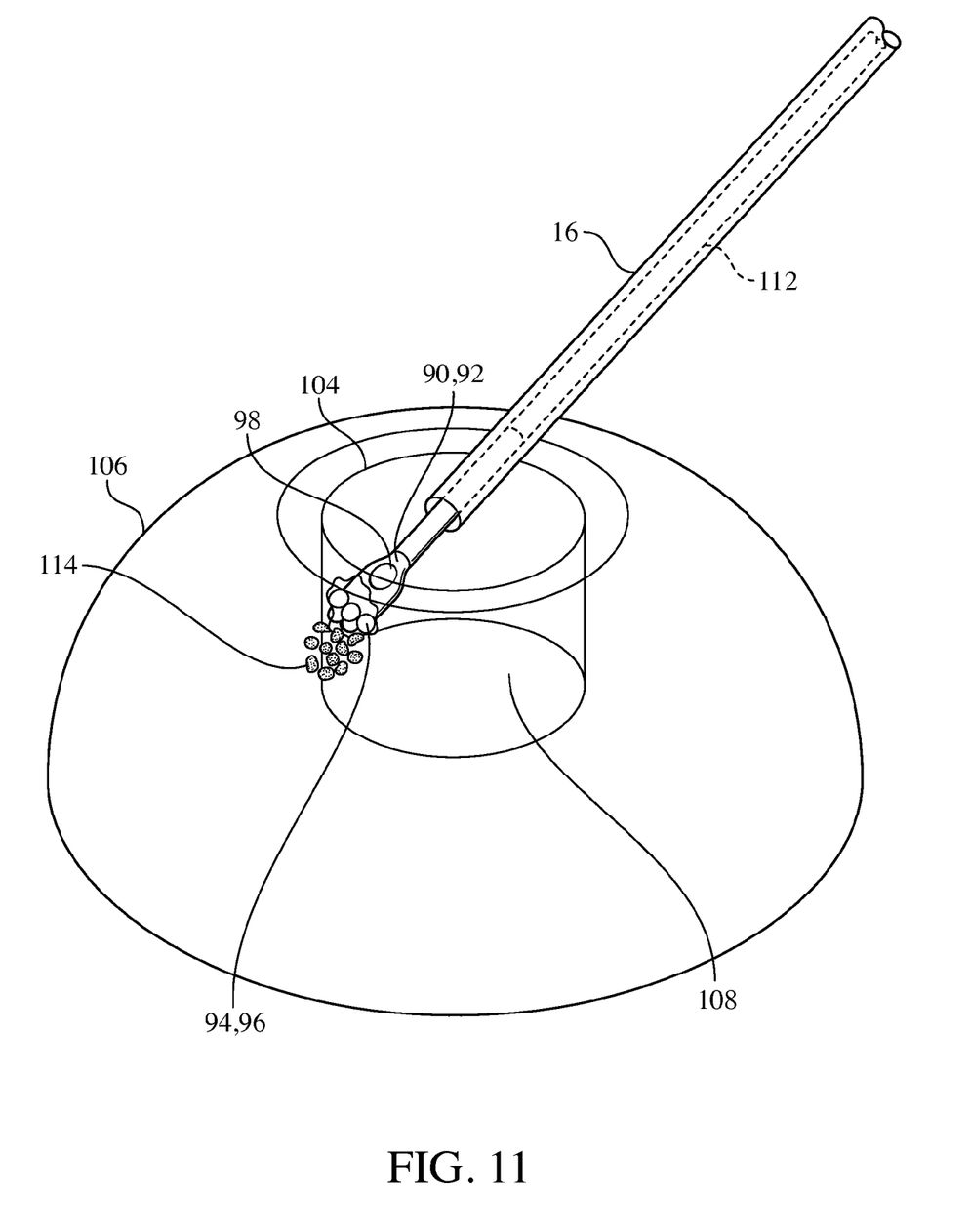
FIG. 11 is an isometric view of a Mulberry tip in accordance with the invention breaking up a tissue peripheral wall (the tissue peripheral wall arising from the peripheral effect an laser energy beam on tissue) that can be pushed more easily than the smooth, rounded tip of FIG. 10 into the soft tissue of the cortex to start aspirating.
Figures 12, 13:
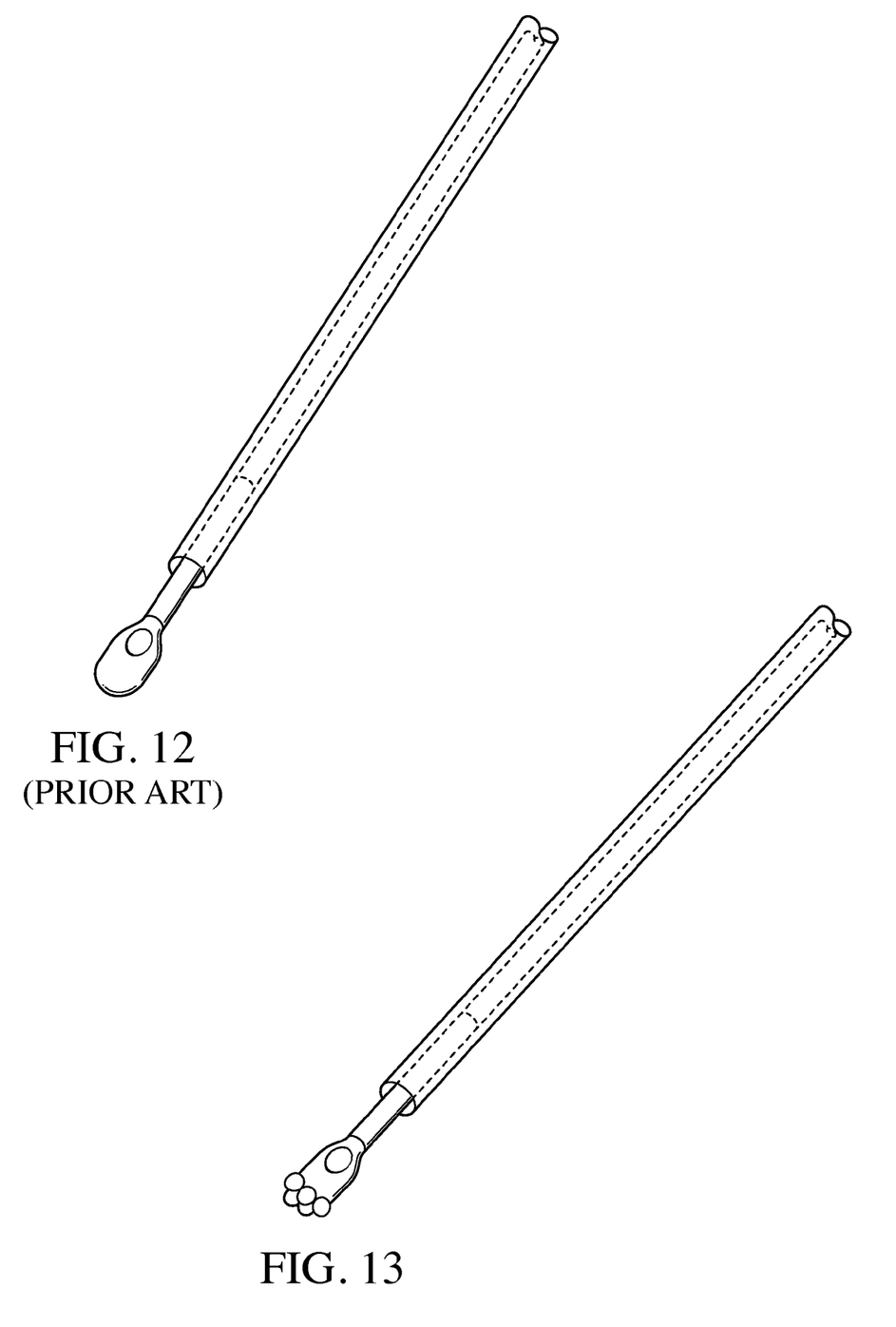
FIGS. 12-13 are isometric views of side-by-side comparison of the Mulberry tip aspiration/irrigation tool of FIG. 11 and the conventional smooth, rounded tip aspiration/irrigation tool of FIG. 10.

The Femto laser is operated to chop or cut the cortex as shown in FIG. 9 and subsequently aspiration is carried out via a suction port 98 to remove the cortex. The mulberry tip 90, 92 used in the manner of FIG. 11 disrupts soft cortical material better than can be done for smoothly, rounded conventional aspiration/irrigation tips 100 used in the manner of FIG. 10. A side-by-side comparison of the surgical tools of FIGS. 10 and 11 are set forth in FIGS. 12 and 13.

Initially, a Femto laser beam creates a circular opening in the anterior capsule of the cataract. This circular opening is defined by an edge 104 of the capsule following previous capsularhesis (see FIG. 9).

The Femto laser beam 102 is then directed to scan a grid pattern as it passes through the circular opening defined by the edge 104 to core out the cataract contents 106 contained within the capsular bag and chops the cataract contents 106 (that constitutes the nucleus of the cataract) into chunky pieces 110 of fragmented, deconstructed nucleus) but leaves a smooth, peripheral wall 108 that is more viscous than the softer, adjacent cortical tissue. The smooth, peripheral wall 108 borders around the outer periphery of the energy beam from the laser and lies adjacent to softer, cortical tissue that beyond the smooth, peripheral wall. Indeed, the smooth, peripheral wall is in a somewhat glossy, coagulated state and may be considered an interface constituted by a cylindrical zone of coagulative remnants of cortical material. One might analogize the effect of the laser beam going through the cataract tissue with that of a pineapple core: the laser beam cubes the nucleus into small pieces but leaves the smooth, peripheral wall somewhat coagulated.

Figure 10:
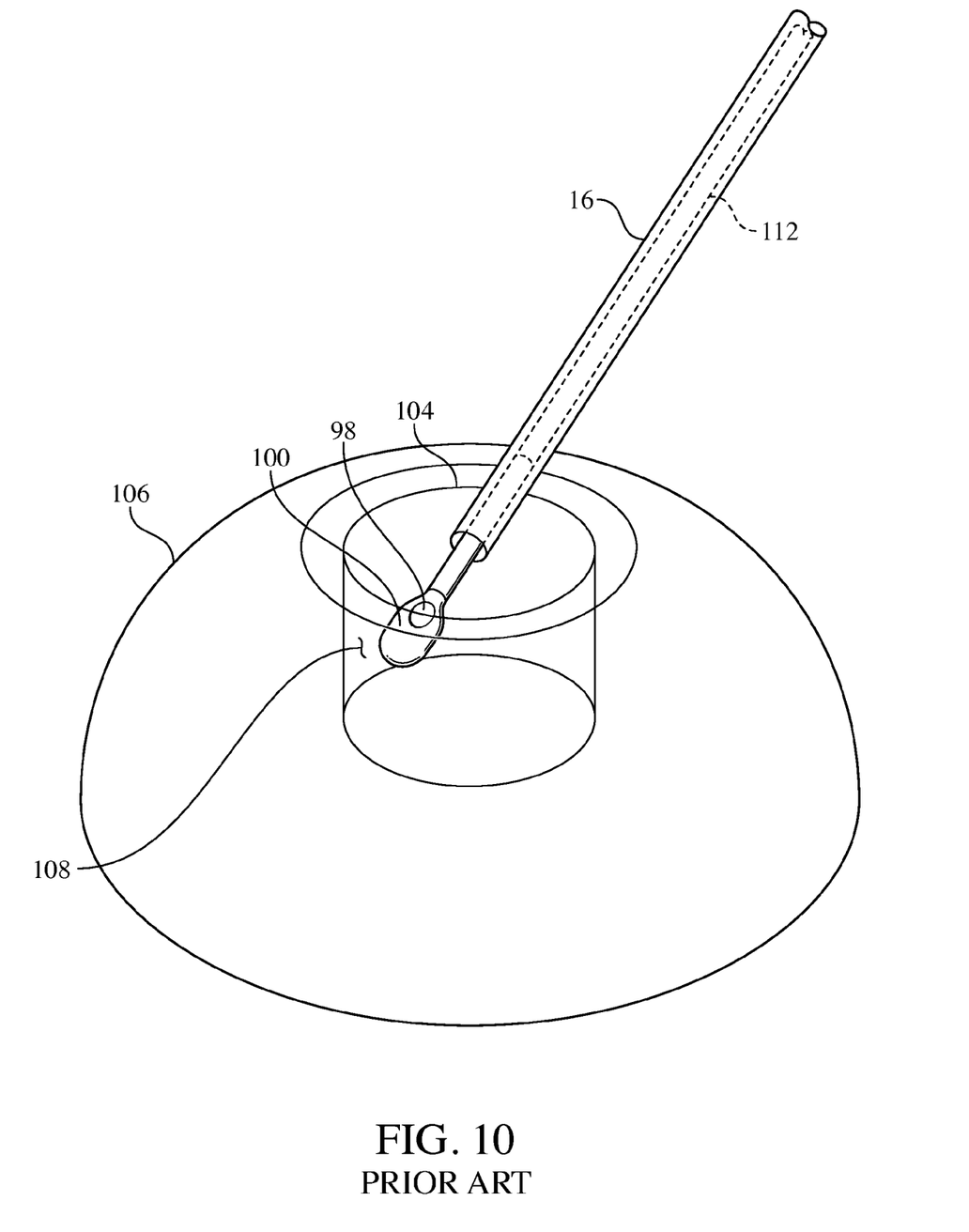
FIG. 10 is an isometric view of a conventional smooth, rounded tip having difficulty getting across a tissue peripheral wall (peripheral wall arising from the peripheral effect of an laser energy beam on tissue) in an effort to enter soft cortex for the purpose of aspirating.

Turning to FIG. 10, a conventional aspiration-irrigation tool is shown having a conventional, smooth rounded tip 100 whose proximal end is secured to a distal end of an aspiration tube 112 in any conventional manner (such as with engaging screw threads or friction fit). One can appreciate that the rounded distal end of the conventional smooth, rounded tip 100 renders it difficult for it to grasp the cortex when brought into contact with the wall of the smooth cylinder.

In a conventional manner, suction is imparted to the hollow tube 112 to suck in cut tissue through the suction port 98. In a conventional manner, the proximal end of the smooth rounded tip 100 is secured to a distal end of a hollow aspiration tube 112, such as with engaging screw threads or is friction fit as the case may be. There is also a surrounding concentric sleeve 16 for irrigating the region in the eye while aspiration is being carried out by directing irrigation fluid to flow in the space between the inner surface of the surrounding concentric sleeve 16 the outer surface of the hollow aspiration shaft 112.

Turning to FIG. 11, the mulberry tip 90, 92 of the present invention has no sharp edges—just rounded, surface protrusions 94, 96 separated from each other by gaps or recesses. In a conventional manner, the proximal end of the mulberry tip 90, 92 is secured to a distal end of a hollow aspiration tube 112, such as with engaging screw threads or friction fit as the case may be. There is also a surrounding concentric sleeve 16 for irrigating the region in the eye while aspiration is being carried out by directing irrigation fluid to flow in the space between the inner surface of the surrounding concentric sleeve 16 the outer surface of the hollow aspiration shaft 112.

Under manual force of sufficient magnitude being imparted to the mulberry tip 90, 92, the mulberry tip 90, 92 is urged against a smooth, peripheral wall 108 to wedge cortical tissue of the smooth, peripheral wall 108 into the gaps or recesses that are between neighboring ones of the rounded, surface protrusions 94, 96. The mulberry tip 90, 92 readily and easily scores and breaks up the smooth, peripheral wall 108 into crumbled, cortical pieces 114 by virtue of the collective action of the rounded surface protrusions 94, 96 that are separated from each other by the gaps or recesses (in effect defining indentations between neighboring ones of the rounded, surface protrusions 94, 96).

The rounded, surface protrusions 94, 96 resemble a cobblestone layout when viewed from the front end so they can wedge in and loosen cortex tissue that is of a consistency of cream cheese (or in any event more viscous than the adjacent, softer cortex tissue). The loosened cortex tissue is then aspirated into the suction port 98 to enter and pass through the base tube and to reach the hollow aspiration tube 112. The base tube lies between the surface port 98 and the hollow aspiration tube 112 and is in the vicinity of where the reference line for 90, 92 touches in FIG. 11.

The soft, fluffy cortex can then right away be sucked into the suction port 98 and thus be removed—in effect speeding up the cortical removal time over that where the conventional smoothly, rounded tip design is used. Indeed, the protrusions are configured, by virtue of their rounded surfaces separated from each other by gaps or recesses 95, to collectively and cooperatively engage with epinucleus cortical material under manual pressure and guidance to divide cortical fibers of the epinucleus cortical material.

The mulberry tip 90, 92 has a base tube and is elongated between proximal and distal ends and has the suction port 98 spaced from the proximal and distal ends. However, the base tube is hollow from the port to the proximal end, but need not be hollow all the way to the distal end. Indeed, the protrusions are arranged at the distal end.

The proximal end connects to the hollow shaft 112 in an airtight manner sufficient to enable a suction force, which is imparted within the hollow shaft 112, to suck divided cortical fibers of epinucleus cortical material into the port and thereafter flow through the hollow of the mulberry tip 90, 92 to enter the hollow of the hollow shaft.

Both the hollow shaft 112 and the hollow base (between the suction port 98 and the proximal end) are constructed of materials sufficient to avoid collapsing (that would impede or block suction) upon being subjected to the suction force that is of a magnitude necessary for the divided cortical fibers to suck into the port and thereafter flow through the hollow of the mulberry tip 90, 92 to enter the hollow of the hollow shaft.

Any of the "capsule friendly" tips as depicted in all the embodiments of the present invention may be used as the irrigation-aspiration tips for all models and makes of conventional irrigation-aspiration handpieces utilizing in phacoemulsification consoles by conventional manufacturers. The choice of material for the "capsule friendly" tips of any of the embodiments of the present invention may include that of metal or hardened silicone.

While the foregoing description and drawings represent the preferred embodiments of the present invention, it will be understood that various changes and modifications may be made without departing from the scope of the present invention.

What is claimed is:

1. A capsule friendly surgical tool, comprising a tip having proximal and distal ends with a hollow base extending between the proximal end of the tip and a suction port, the tip having a plurality of protrusions at the distal end of the tip each separated from each other by gaps or recesses of dimensions sufficient to wedge in and loosen cortex tissue in response to sufficient manual force being imparted to the tip, each of the protrusions having curved external surfaces entirely free of sharp edges, both the hollow base and the suction port being spaced from the distal end of the tip, the proximal end of the tip being configured to fit to a hollow shaft in an airtight manner sufficient for a suction force imparted into the hollow of the hollow shaft to suck divided cortical fibers of an epinucleus cortical material into the suction port to flow through the hollow of the hollow base to reach the hollow of the hollow shaft, the protrusions being configured to collectively and cooperatively engage with the epinucleus cortical material to, under manual pressure and guidance, divide the cortical fibers of the epinucleus cortical material, both the hollow shaft and the hollow base being constructed of materials sufficient to avoid their collapse upon being subjected to the suction force that is of a magnitude necessary for the divided cortical fibers to suck into the suction port to reach the hollow of the hollow shaft via the hollow of the hollow base.

2. The capsule friendly surgical tool of claim 1, wherein the base extends between the proximal and distal ends of the tip uniformly about a centerline passing through a hollow of the base, the protrusions being configured in a manner symmetric with each other and concentric with the centerline.

3. The capsule friendly surgical tool of claim 1, wherein each of the protrusions has rounded surfaces.

4. A method of operating a capsule friendly surgical tool, comprising providing a tip having proximal and distal ends, the tip having a hollow base that is hollow and extends from the proximal end of the tip to a suction port, the tip having a plurality of protrusions at the distal end of the tip each separated from each other by gaps or recesses of sufficient dimension to wedge in and loosen cortex tissue in response to application of sufficient manual force imparted to the tip, each of the protrusions having curved external surfaces entirely free of sharp edges, both the hollow base and the suction port being spaced from the distal end of the tip, the proximal end of the tip being configured to fit to a hollow shaft that is hollow in an airtight manner sufficient for a suction force imparted into the hollow of the hollow shaft to suck divided cortical fibers of an epinucleus cortical material into the suction port to flow through the hollow of the hollow base to reach the hollow of the hollow shaft, fitting the proximal end of the tip to the hollow shaft in the airtight manner; and collectively and cooperatively engaging the protrusions, under manual pressure and guidance, with the epinucleus cortical material to divide cortical fibers of the epinucleus cortical material, both the hollow shaft and the hollow base being constructed of materials sufficient to avoid their collapse upon being subjected to the suction force that is of a magnitude necessary for the divided cortical fibers to suck into the suction port to reach the hollow of the hollow shaft via the hollow base.

* * * * *